United States Patent [19]

Watson

[11] 4,132,602

[45] Jan. 2, 1979

[54] POLYMERIZATION INHIBITOR FOR VINYL AROMATIC COMPOUNDS

[75] Inventor: James M. Watson, Big Spring, Tex.

[73] Assignee: Cosden Technology, Inc., Big Spring, Tex.

[21] Appl. No.: 854,410

[22] Filed: Nov. 23, 1977

[51] Int. Cl.² .............................................. B01D 3/34
[52] U.S. Cl. ......................................... 203/9; 203/65; 260/666.5; 260/669 A
[58] Field of Search ...................... 260/666.5, 669 A; 203/9, DIG. 7, 65

[56] References Cited

U.S. PATENT DOCUMENTS

| | | | |
|---|---|---|---|
| 3,366,702 | 1/1968 | Moriarty | 203/9 |
| 3,988,212 | 10/1976 | Watson | 203/9 |
| 4,033,829 | 7/1977 | Higgins et al. | 203/9 |
| 4,086,147 | 4/1978 | Watson | 203/9 |

*Primary Examiner*—Hiram H. Bernstein

[57] ABSTRACT

Disclosed is a process for the distillation of readily polymerizable vinyl aromatic compounds which comprises subjecting such compounds to distillation conditions in the presence of an effective amount of a halo-6-nitro-p-cresol as a polymerization inhibitor.

11 Claims, No Drawings

POLYMERIZATION INHIBITOR FOR VINYL AROMATIC COMPOUNDS

BACKGROUND OF THE INVENTION

The present invention relates to a process for the distillation of readily polymerizable vinyl aromatic compounds, and more especially, to a process for the distillation of styrene, substituted styrene, divinylbenzene, and mixtures thereof, wherein the amount of said materials polymerized during distillation is reduced over an extended period of time, wherein the material accumulating in the bottom or reboiler area of the distillation apparatus is essentially free from significant sulfur contamination, and wherein the rate of throughput for a given distillation apparatus may be increased over the rate at which such apparatus may be operated in accordance with conventional methods.

It is well known that vinyl aromatic compounds such as monomeric styrene, lower alkylated styrene, e.g., alpha-methyl styrene, and the like polymerize readily, and furthermore, that the rate of polymerization increases with increasing temperature. Inasmuch as vinyl aromatic compounds produced by common industrial methods contain impurities, these compounds must be subjected to separation and purification processes in order to be suitable for most types of further industrial use. Such separation and purification is generally accomplished by distillation.

In order to prevent polymerization during distillation of vinyl aromatic compounds, various types of known polymerization inhibitors have been employed in connection with prior art distillation processes. For example, common inhibitors useful for inhibiting the polymerization of vinyl aromatic compounds under distillation conditions include 4-tert-butyl-catechol (TBC) and hydroquinone. Additionally, sulfur has been widely employed as a polymerization inhibitor during the distillation of various vinyl aromatic compounds. However, while sulfur provides a reasonably effective inhibitor, its use in such distillation processes results in a highly significant disadvantage, namely, there is formed in the reboiler bottoms of the distillation column a valueless waste material highly contaminated with sulfur. This waste material furthermore represents the significant problem of pollution and/or waste removal.

Although many compounds are effective for inhibiting the polymerization of vinyl aromatic compounds under differing conditions, e.g., storage, other purification techniques, etc., for a number of reasons which are not entirely understood in view of the diverse and unpredictable results obtained, only extremely few of these compounds have proved to be of any real utility for inhibiting vinyl aromatic polymerization under distillation conditions. In a typical distillation process for vinyl aromatic compounds utilizing a polymerization inhibitor, the mixture of material to be distilled is generally contacted with the chemical polymerization inhibitor prior to being subjected to distillation conditions in the distillation apparatus. It remains as a significant problem today that the amount of polymer formed in the distillation apparatus and in the high purity product recovered therefrom is substantially higher than desired, and occasionally, that complete polymerization occurs inside of the distillation apparatus. For example, in the process of distilling crude styrene (a mixture containing, inter alia, styrene, ethylbenzene and tars) to obtain high purity styrene, even when inhibited with sulfur and TBC, a styrene product is obtained which contains significant quantities of polymer which are difficult to separate from the product and are detrimental to the use of such styrenes. Furthermore, the material removed from the bottom or reboiler area of the distillation apparatus is a highly polluting sulfur-containing waste material which must be disposed.

Accordingly, there exists a strong need for a polymerization inhibitor which will effectively prevent the polymerization of vinyl aromatic compounds during distillation thereof, without the attendant problem of generating copious quantities of noxious waste.

SUMMARY OF THE INVENTION

It is therefore an object of the present invention to provide a new and improved process for the distillation of readily polymerizable vinyl aromatic compounds.

A further object of the present invention is to provide a new and improved process for the distillation of readily polymerizable vinyl aromatic compounds, which process results in higher recovery of high purity unsaturated vinyl aromatic compounds and concomitantly in the production of less undesirable by-products.

Yet another object of the invention resides in the provision of a new and improved process for the distillation of vinyl aromatic compounds which avoids the production of a highly polluting, contaminated bottom or reboiler residue.

It is also an object of the present invention to provide a new and improved process for the distillation of vinyl aromatic compounds which permits the distillation apparatus to be operated at an increased rate of throughput without a reduction in efficiency.

It is yet another object of the present invention to provide a new and improved process for the distillation of vinyl aromatic compounds which provides all of the foregoing enumerated advantages in an elevated temperature distillation process.

In accomplishing the foregoing objects, there has been provided in accordance with the present invention a process for the distillation of a readily polymerizable vinyl aromatic compound comprising subjecting such compound to distillation conditions in the presence of an effective amount of a 2-halo-6-nitro-p-cresol to inhibit polymerization of the vinyl aromatic compound under the distillation conditions. In one aspect of the process according to the invention, the inhibitor is simply introduced into the distillation system by injection into the reboiler area of the distillation apparatus, or alternatively, by injection into the incoming stream of compound to be purified. It is one salient feature of the present invention that the mode of introducing and metering the amount of polymerization inhibitor is considerably simplified due to the ease of metering the material and due to the simplicity of the equipment necessary therefor, as the inhibitor material is soluble in solvents compatible with the styrene feed, including styrene itself.

The amount of the 2-halo-6-nitro-p-cresol necessary to inhibit polymerization of the vinyl aromatic compounds may vary over a broad range depending upon various factors of the distillation process as, for example, temperature, amount of reflux, if any, pressure, residence time, etc. Typically, however, it has been found that an amount of inhibitor between about 25 ppm and 1000 ppm is sufficient to substantially inhibit polymerization of vinyl aromatic compounds under normal distillation conditions, e.g., at about 115° C.

Through the use of the process according to the present invention, the amount of polymerization occurring within the distillation apparatus is significantly reduced in comparison to conventionally employed methods. In addition, the amount of desired distillation product is increased in proportion to the decrease in the amount of polymer formation. Also, the rate of operation of a given distillation apparatus may be increased over and above the rate of operation for the same apparatus utilizing conventional inhibitors. Still further, the material accumulating in the bottom or reboiler area of the distillation apparatus can be reused, e.g., for its fuel value or for reprocessing, which is a distinct advantage over conventional methods utilizing sulfur as a polymerization inhibitor which methods produce a highly polluting waste material in the reboiler area. Furthermore, it has also been found that any polymeric material inadvertently formed during the process of the invention presents fewer problems in connection with fouling of the distillation apparatus.

Further features, objects and advantages of the invention will become apparent from the detailed description which follows and from the claims.

DETAILED DESCRIPTION OF PREFERRED EMBODIMENTS

The distillation process of the present invention employs a 2-halo-6-nitro-p-cresol as a polymerization inhibitor during the distillation of vinyl aromatic compounds, and especially styrene-containing compounds, for the purification thereof. The distillation process may be conducted over wide-ranging parameters including reduced-pressure distillation (i.e., vacuum distillation), and atmospheric distillation (i.e., open to the atmosphere), and over a fairly broad range of temperatures from about 65° C. to about 150° C. One of the most significant advantages of the invention, in addition to the broad operative ranges of pressure and temperature and the reduction of unwanted polymerization, is that the use of sulfur in the distillation system may be avoided, thus obviating the production of noxious by-products and the attendant problem of their disposal for further processing.

The particular polymerization inhibitors of the present invention have the following general formula:

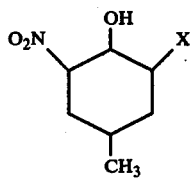

wherein X is a halogen radical. Thus, in accordance with the present invention, the polymerization inhibitor may be 2-chloro-6-nitro-p-cresol, 2-bromo-6-nitro-p-cresol, 2-iodo-6-nitro-p-cresol or 2-fluoro-6-nitro-p-cresol or mixtures of these. However, the preferred polymerization inhibitors of the present invention are those of the above formula wherein X is selected from the group consisting of the chloro, bromo and iodo radicals. The most preferred of these inhibitors is the 2-iodo-6-nitro-p-cresol.

The inhibitor of the present invention may be added to the incoming stream of vinyl aromatic material, into the reboiler area of the distillation apparatus, or at other suitable points, either in solid or liquid form.

The distillation technique of the process of the present invention is suitable for use in virtually any type of distillative separation of a readily polymerizable vinyl aromatic compound from a mixture wherein the compound is subjected to temperatures above room temperature. Surprisingly, the process of the present invention has been found adaptable to reduced pressure distillation techniques (vacuum distillation) as well as atmospheric distillation techniques (i.e., open to the atmosphere).

The amount of polymerization inhibitor added may vary over a wide range depending upon the conditions of distillation. Generally, the degree of stabilization is proportional to the amount of inhibitor added. In accordance with the present invention, it has been found that inhibitor concentrations generally between about 25 and about 1,000 ppm have generally provided suitable results, depending primarily upon the temperature of the distillation mixture and the degree of inhibition desired.

During distillation of the styrene-containing mixtures, the temperature of the reboiler is preferably maintained from about 65° C. to about 150° C. Preferred, however, is a temperature within the range of from about 90° C. to about 143° C. Under such conditions, in a distillation apparatus having a distillation zone containing from about 50 to 100 distillation stages, inhibitor concentrations of from about 20 to about 400 ppm are suitable, whereas concentrations of from about 50 to about 400 ppm are preferred. Obviously, amounts of inhibitor greater than those specified hereinabove may be employed, although the advantages of adding the additional inhibitor are not significant and are outweighed by the corresponding increase in the cost.

The polymerization inhibitors of the present invention may be introduced into the distillation apparatus in any convenient manner which permits efficient distribution of the inhibitor throughout the apparatus. Thus, the inhibitor may be added as a solid or, optionally, dissolved in an appropriate carrier, e.g., styrene, and simply injected through conventional metering systems. The solid may be added to the incoming stream of feed material, into the reboiler area of the distillation column, or at any other convenient location.

Since the inhibitor is gradually depleted during operation, it is generally necessary to maintain the appropriate amount of inhibitor in the distillation apparatus by adding inhibitor during the course of the distillation process. Such addition may be carried out either on a generally continuous basis or it may consist of intermittent charging of inhibitor into the distillation system. The means by which the maintenance of the necessary inhibitor concentration is carried out is of no particular importance provided the concentration of inhibitor is maintained above the minimum required level.

Use of the polymerization inhibitors of the present invention enables the distillation apparatus to operate at an increased rate as opposed to conventional prior art processes since the inhibitor of the present invention is more efficient than conventional inhibitors, and will thus permit higher distillation temperatures at high pressures. In this manner, the rate of distillation may be increased without increasing the amount of polymerization which has been deemed to be acceptable in accordance with conventional distillation procedures.

When the process of the present invention is utilized, the bottoms material which accumulates during the distillation process can be drawn off and utilized for its heating value or for reprocessing. As there is no sulfur contamination, this represents another significant advantage in comparison to conventional processes for distillation of vinyl aromatic compounds which employ sulfur as the polymerization inhibitor, or sulfur in combination with other chemical polymerization inhibitors.

Upon recovery of the distillation product obtained from the process of the present invention, it is found that a higher percentage of the pure readily polymerizable styrenic compound is recovered in an unpolymerized state, and that the inhibitor in no manner derrogates from subsequent polymerization of the recovered product. Furthermore, it has been noted that the polymeric products which are formed during the distillation process of the invention are of such a character that there is less fouling or plugging of the apparatus as compared with many conventional inhibitors.

In order to more fully describe the present invention, the following examples are presented which are intended to be merely illustrative and not in any sense limitative of the invention:

EXAMPLE I

Forty-seven and one-half grams of distilled TBC free styrene is charged to a 100 milliliter reaction flask which is fitted with magnetic stirrers and septum closures. 2-chloro-6-nitro-p-cresol inhibitor is added to the styrene charge in an amount of 50° ppm relative to the weight of the styrene and the flask heated by a stirred oil bath to 115° C., controlled within ± 2° C.

Inhibitor effectiveness is monitored qualitatively by methanol dilution of samples withdrawn from the reaction flask using a hypodermic syringe. Thus, samples are withdrawn and tested by combining 1 milliliter samples with 3 milliliters of methanol and examining for turbidity. Such tests indicate that this level of 2-chloro-6-nitro-p-cresol provides an inhibiting effectiveness such that after approximately five hours only 4.1% polymer is found to have formed.

EXAMPLE II

Forty-seven and one-half grams of distilled TBC free styrene was charged to a 100 milliliter reaction flask as described in Example I. To this was added 500 ppm of 2-bromo-6-nitro-p-cresol as an inhibitor. The flask was heated and sampled as described in Example I. The amount of polymer formed at 5 hours was 4.1 wt. percent.

EXAMPLE III

Example II was again repeated with the exception that 2-iodo-6-nitro-p-cresol was substituted for the inhibitor used in said Example II and the test was run for only 4 hours. At the end of such 4 hour period, only 2.6% by weight of polymer had formed.

EXAMPLE V

Example IV was repeated with the exception that the run was allowed to continue for 6 hours. The amount of polymer formed at various intervals during such 6 hours were as follows:

1.5 hours:0.9 wt. %
3.0 hours:2.0 wt. %
4.5 hours:3.6 wt. %
6.0 hours:6.2 wt. %

EXAMPLE VI

To demonstrate the unexpectedness of the results presented above in Examples I through V, a series of additional runs were made under the same conditions as above except as to time of duration. The compounds tested were other halogen substituted phenolic compounds. The compounds and results are set forth below:
2,3,5,6-tetrabromo-p-cresol:ineffective
2,6,-dibromo-4-methylphenol:ineffective
2-bromo-4-methylphenol:ineffective
2-chloro-5-nitro-p-cresol:very slight activity, coagulation with methanol after 2 hours The foregoing examples demonstrate the highly effective inhibition of polymerization of styrene when a 2-halo-6-nitro-p-cresol inhibitor is employed. The process incorporating the 2-halo-6-nitro-p-cresol inhibitor is capable of proceeding under atmospheric or subatmospheric conditions. However, while the invention has been described in terms of various preferred embodiments, the skilled artisan will readily appreciate that various other modifications, omissions, substitutions, or changes may be made without departing from the spirit thereof. Accordingly, it is intended that the scope of the invention be limited solely by the following claims.

What is claimed is:
1. A process for the distillation of a readily polymerizable vinyl aromatic compound, which comprises subjecting such compound to distillation conditions in the presence of an effective amount of a 2-halo-6-nitro-p-cresol as a polymerization inhibitor.
2. The process as defined by claim 1, wherein said 2-halo-6-nitro-p-cresol polymerization inhibitor is continuously added to said vinyl aromatic compound.
3. The process as defined in claim 1, wherein said vinyl aromatic compound comprises styrene.
4. The process as defined by claim 1, wherein said inhibitor is present in an amount of from about 25 ppm to about 1000 ppm.
5. The process as defined by claim 1, wherein said distillation conditions comprise a temperature between about 65° and 150° C.
6. The process as defined by claim 5, wherein said temperature is between about 90° and 143° C.
7. The process of claim 1, wherein said inhibitor is 2-chloro-6-nitro-p-cresol.
8. The process of claim 1, wherein said inhibitor is 2-bromo-6-nitro-p-cresol.
9. The process of claim 1, wherein said inhibitor is 2-iodo-6-nitro-p-cresol.
10. The process of claim 1, wherein said vinyl aromatic compound comprises alpha-methyl styrene.
11. The process of claim 1, wherein said vinyl aromatic compound comprises divinylbenzene.

* * * * *